(12) United States Patent
Kim et al.

(10) Patent No.: US 10,859,492 B2
(45) Date of Patent: Dec. 8, 2020

(54) OPTICAL SENSOR AND METHOD OF OPERATING THE OPTICAL SENSOR

(71) Applicant: SAMSUNG ELECTRONICS CO., LTD., Suwon-si (KR)

(72) Inventors: Sangkyu Kim, Yongin-si (KR); Kunsun Eom, Seoul (KR); Myounghoon Jung, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 17 days.

(21) Appl. No.: 15/078,462

(22) Filed: Mar. 23, 2016

(65) Prior Publication Data
US 2017/0059482 A1  Mar. 2, 2017

(30) Foreign Application Priority Data

Aug. 28, 2015  (KR) .................. 10-2015-0121828

(51) Int. Cl.
*G01N 21/55* (2014.01)
*G01N 33/483* (2006.01)
(Continued)

(52) U.S. Cl.
CPC .......... *G01N 21/55* (2013.01); *A61B 5/0071* (2013.01); *A61B 5/0075* (2013.01); *G01N 21/255* (2013.01); *G01N 21/31* (2013.01); *G01N 21/59* (2013.01); *G01N 21/645* (2013.01); *G01N 21/6428* (2013.01); *G01N 33/483* (2013.01);
(Continued)

(58) Field of Classification Search
CPC .. G01N 21/59; G01N 21/6428; G01N 33/483; G01N 21/55; G01N 21/255; A61B 5/0071; A61B 5/0075
See application file for complete search history.

(56) References Cited

U.S. PATENT DOCUMENTS 4,678,326 A    7/1987  Harjunmaa
5,371,016 A *  12/1994  Berndt ............... G01N 21/6428
                                                  250/461.2
(Continued)

FOREIGN PATENT DOCUMENTS

CN    101357065 A    2/2009
EP    0242725 A2    10/1987
(Continued)

OTHER PUBLICATIONS

Communication dated Feb. 1, 2017, issued by the European Patent Office in counterpart European Application No. 16171117.1.
(Continued)

*Primary Examiner* — Brian R Gordon
*Assistant Examiner* — Dwan A Gerido
(74) *Attorney, Agent, or Firm* — Sughrue Mion, PLLC

(57) ABSTRACT

An optical sensor and a method of operating the optical sensor are provided. The optical sensor includes a light source configured to emit a light, and a path adjuster configured to adjust a traveling path of the light to reflect the light at a first time, and allow the light to pass through the path adjuster at a second time. The optical sensor further includes a light receiver configured to receive a reference light among the reflected light, and receive, among the light passing through the path adjuster, a measurement light related to a target material.

19 Claims, 12 Drawing Sheets

(51) Int. Cl.
*G01N 21/59* (2006.01)
*G01N 21/64* (2006.01)
*A61B 5/00* (2006.01)
*G01N 21/25* (2006.01)
*G01N 21/31* (2006.01)
*G02B 26/08* (2006.01)
*G02B 26/02* (2006.01)
*G01N 21/359* (2014.01)
*G02B 26/00* (2006.01)

(52) U.S. Cl.
CPC ... *G01N 21/359* (2013.01); *G01N 2021/6471* (2013.01); *G01N 2201/0221* (2013.01); *G01N 2201/066* (2013.01); *G01N 2201/067* (2013.01); *G01N 2201/13* (2013.01); *G02B 26/005* (2013.01); *G02B 26/026* (2013.01); *G02B 26/08* (2013.01)

(56) References Cited

U.S. PATENT DOCUMENTS

| | | | |
|---|---|---|---|
| 5,770,454 A | 6/1998 | Essenpreis et al. | |
| 5,940,150 A | 8/1999 | Faris et al. | |
| 6,070,093 A * | 5/2000 | Oosta | A61B 5/0095 356/39 |
| 6,400,973 B1 * | 6/2002 | Winter | A61B 5/1495 600/323 |
| 2006/0119916 A1 * | 6/2006 | Sutherland | G02F 1/13342 359/34 |
| 2006/0269896 A1 * | 11/2006 | Liu | A61C 7/00 433/29 |
| 2009/0036783 A1 | 2/2009 | Kishima | |
| 2011/0299089 A1 | 12/2011 | Wang et al. | |
| 2014/0339428 A1 | 11/2014 | O'Brien et al. | |
| 2015/0025341 A1 | 1/2015 | Sakota et al. | |
| 2016/0310027 A1 * | 10/2016 | Han | A61B 5/02427 |

FOREIGN PATENT DOCUMENTS

| | | |
|---|---|---|
| JP | 2010185694 A | 8/2010 |
| JP | 2013164372 A | 8/2013 |
| KR | 20000075762 A | 12/2000 |
| KR | 1020140105956 A | 9/2014 |

OTHER PUBLICATIONS

Communication dated Mar. 16, 2020, from the State Intellectual Property Office of People's Republic of China in counterpart Application No. 201610404872.3.

* cited by examiner

OPTICAL SENSOR AND METHOD OF OPERATING THE OPTICAL SENSOR

CROSS-REFERENCE TO RELATED APPLICATION

This application claims priority from Korean Patent Application No. 10-2015-0121828, filed on Aug. 28, 2015, in the Korean Intellectual Property Office, the disclosure of which is incorporated herein in its entirety by reference.

BACKGROUND

1. Field

Apparatuses and methods consistent with exemplary embodiments relate to an optical sensor and a method of operating the optical sensor.

2. Description of the Related Art

Interest in healthcare has increased with the development of medical science and extension of the average lifespan. Also, interest in medical equipment has increased as well to extend not only to various medical equipment used in hospitals or health examination organizations, but also to middle- or small-sized medical equipment provided in public organizations and compact medical equipment and health-care apparatuses that may be kept or carried by individuals.

An invasive measurement method has been widely used in conjunction with medical equipment to perform various medical tests. An invasive measurement method may be performed, for example, by sampling blood of an object and measuring and analyzing the sampled blood. By measuring a density of a substance in blood, a health state relative to the substance may be obtained. However, in the invasive measurement method, blood sampling is painful, and a reagent reacting to a substance of blood and a color iodometric assay are inconveniently used for blood analysis.

Currently, a method of detecting biological information via a non-invasive method is under development. However, the non-invasive method has a high error probability compared to the invasive method.

SUMMARY

Exemplary embodiments may address at least the above problems and/or disadvantages and other disadvantages not described above. Also, the exemplary embodiments are not required to overcome the disadvantages described above, and may not overcome any of the problems described above.

One or more exemplary embodiments provide a portable optical sensor and a method of operating the portable optical sensor.

According to an aspect of an exemplary embodiment, there is provided an optical sensor including a light source configured to emit a light, and a path adjuster configured to adjust a traveling path of the light to reflect the light at a first time, and allow the light to pass through the path adjuster at a second time. The optical sensor further includes a light receiver configured to receive a reference light among the reflected light, and receive, among the light passing through the path adjuster, a measurement light related to a target material.

Each of the reflected light and the light passing through the path adjuster may be among the emitted light.

The measurement light may be a light that is reflected by the target material among the light passing through the path adjuster.

The measurement light may be a light passing through the target material among the light passing through the path adjuster.

The measurement light may be a light that is emitted from a marker coupled to the target material based on the light passing through the path adjuster.

A center wavelength of the light emitted from the marker may be different from a center wavelength of the light emitted from the light source.

The optical sensor may further include a processor configured to obtain information of the target material based on the reference light and the measurement light.

The processor may be further configured to normalize the measurement light based on the reference light, and obtain the information of the target material based on the normalized measurement light.

The normalized measurement light may be a ratio of an intensity of the measurement light to an intensity of the reference light.

The first time and the second time may be different.

The light receiver may be further configured to alternately receive the reference light and the measurement light.

The path adjuster may be further configured to adjust at least one among a reflectance and a transmittance of the path adjuster based on an electric signal.

The path adjuster may be further configured to adjust the reflectance of the path adjuster to be greater than the transmittance of the path adjuster in response to a first electric signal, and adjust the reflectance of the path adjuster to be less than the transmittance of the path adjuster in response to a second electric signal different from the first electric signal.

The path adjuster may include a first electrode, a second electrode spaced apart from the first electrode, and a reaction portion configured to reflect the emitted light, and allow the emitted light to pass through the reaction portion, based on an electric signal that is applied between the first electrode and the second electrode.

The reaction portion may include at least one among polymer dispersed liquid crystal, twisted nematic liquid crystal, vertical alignment liquid crystal, electrically controlled birefringence liquid crystal, an electrochromic device, a reflection particle including a reflection plate and transparent material, and a polar liquid and a non-polar liquid, the polar liquid being configured to move based on an electrowetting phenomenon.

The path adjuster may be further configured to reflect a part of the emitted light incident on the path adjuster, and allow another part of the incident light to pass through the path adjuster.

The light receiver may include a first light receiver configured to receive the reference light, and a second light receiver configured to receive the measurement light.

The target material may be a material included in skin or blood of an object.

The path adjuster may include a reflection plate configured to pivot around a hinge, and an actuator configured to rotate the reflection plate to reflect the emitted light, and allow the emitted light to pass through the path adjuster, based on an electric signal.

According to an aspect of another exemplary embodiment, there is provided a method of operating an optical sensor including a path adjuster, the method including adjusting a traveling path of a light to reflect the light at a first time, and allow the light to pass through the path adjuster at a second time, using the path adjuster. The method further includes receiving a reference light among the reflected light, and receiving, among the light passing through the path adjuster, a measurement light related to a target material.

The method may further include emitting the light to the path adjuster.

Each of the reflected light and the light passing through the path adjuster may be among the emitted light.

The measurement light may be a light that is reflected from the target material among the light passing through the path adjuster.

The method may further include obtaining information of the target material based on the reference light and the measurement light.

The obtaining may include normalizing the measurement light based on the reference light, and obtaining the information of the target material based on the normalized measurement light.

The normalized measurement light may be a ratio of the measurement light to the reference light.

BRIEF DESCRIPTION OF THE DRAWINGS

The above and/or other aspects will be more apparent by describing exemplary embodiments with reference to the accompanying drawings, in which.

DETAILED DESCRIPTION

Figure 1:
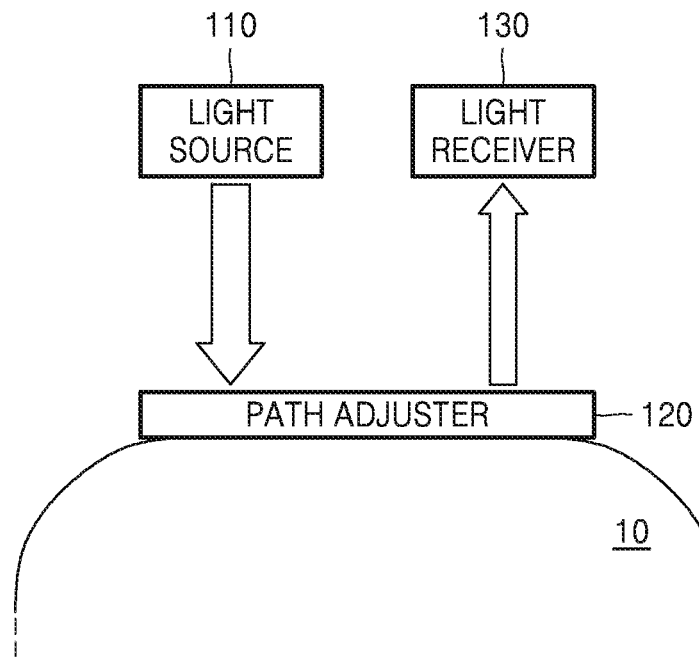
FIG. 1 is a block diagram of an optical sensor according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions may not be described in detail because they would obscure the description with unnecessary detail.

It will be understood that the terms "comprises" and/or "comprising" used herein specify the presence of stated features or components, but do not preclude the presence or addition of one or more other features or components. In addition, the terms such as "unit," "-er (-or)," and "module" described in the specification refer to an element for performing at least one function or operation, and may be implemented in hardware, software, or the combination of hardware and software.

When biological information is detected in a non-invasive method, a spectroscope may be used. A spectroscope may be used to transmit a signal of a wavelength range to an object to detect biological information thereof, and then detect a wavelength of a reflected signal or a peak of the signal. For example, when a wavelength is detected, a component matching the wavelength may be considered to be included in the object. Also, an amount of the matched component may be estimated using a peak value of the wavelength.

For example, in a process of changing an existing large-sized spectroscope to a compact portable spectroscope, calibration of a measurement light using a reference light spectroscope is performed due to generation of heat inside a spectroscope. Because an optical sensor according to an exemplary embodiment measures a reference light and a measurement light using a single device, the measurement light may be conveniently calibrated.

The optical sensor according to an exemplary embodiment may be a portable apparatus, for example, a wearable device. An optical sensor may be configured by any one among a wristwatch type device, a bracelet type device, a ring type device, and a hairband type device, which is equipped with a communication function and a data processing function, or may be a combination of the above-listed devices.

Also, an optical sensor may include a single housing or a plurality of housings. When an optical sensor includes a plurality of housings, a plurality of constituent elements may be connected to one another by wire or wirelessly. For example, an optical sensor that may be worn around a wrist of a user may be divided into a first apparatus receiving light related to a target material and a second apparatus obtaining information about the target material by processing received light. The optical sensor may be included in an apparatus performing other functions, for example, the optical sensor may be a partial structure of a mobile terminal.

FIG. 1 is a block diagram of an optical sensor 100a according to an exemplary embodiment. Referring to FIG. 1, the optical sensor 100a includes a light source 110, a path adjuster 120 adjusting a traveling path of light, and a light receiver 130 receiving a reference light used as a reference among reflected lights from the path adjuster 120 and receiving a measurement light related to a target material 11 (of FIG. 3) among lights passing through the path adjuster 120.

The light source 110 and the light receiver 130 may be provided in an area different from an object 10 with respect to the path adjuster 120. In an exemplary embodiment, the object 10 may be located in a first space, and the light source 110 the light receiver 130 may be located in a second space with respect to the path adjuster 120.

The light source 110 may emit flickering light with a predetermined frequency. The light source 110 may include a semiconductor light-emitting device such as a light emitting diode (LED) or a laser diode (LD), and a gas discharge lamp such as a halogen lamp or a xenon lamp. Also, the light source 110 may be a surface light source having a large light-emitting area and capable of emitting uniform light so that light may be emitted to an area of the object 10. For example, a backlight may be used as the light source 110.

The light emitted from the light source 110 may vary according to types of the object 10 and the target material 11. For example, when the object 10 is a human and the target material 11 is a material in a skin of the object 10, the light source 110 may emit red light or light having a wavelength of a near infrared ray, for example, a center wavelength of about 700 µm to about 1000 µm. The above-described wavelength range is an example, and the light source 110 may emit light having a different wavelength according to the target material 11.

The object 10 may be a human or an animal. However, exemplary embodiments are not limited thereto. The object 10 may be a part of the object 10. For example, the object 10 may be a biological source such as physiological fluid including blood, interstitial fluid, saliva, ocularlens fluid, cerebral spinal fluid, sweat, urine, milk, ascites fluid, raucous, synovial fluid, peritoneal fluid, vaginal fluid, amniotic fluid. However, exemplary embodiments are not limited thereto. The object 10 may be an environment sample for water quality management or soil management, and the type of a sample is not limited.

The target material 11 may be included in the object 10, and may be a material having optical characteristics. The target material 11 may be a material included in the object 10, and may be a material obtained as a material included in the object 10 is combined with a fluorescent material. For example, the target material 11 may be high sensitivity C-reactive protein (hsCRP), MicroCRP, HbA1c, microalbumin, prostate specific antigen (PSA), alpha-fetoprotein (AFP), cardiac troponin I (cTnI), glucose, C-reactive protein (CRP), etc., and a type of the target material 11 is not limited.

The target material 11 may have different absorption, transmission, and reflection with respect to light of a wavelength according to a molecular bonding structure, a shape of a molecule, a potential energy surface (PES), masses of atoms, or vibration coupling. Accordingly, information about the target material 11 may be obtained by recognizing characteristics of the light reflected by or passing through the target material 11.

The light source 110 may emit or irradiate light to the path adjuster 120. The light irradiated to the path adjuster 120 may be reflected by or passing through the path adjuster 120.

The path adjuster 120 may adjust a traveling path of light. The path adjuster 120 may adjust at least one among reflectance and transmittance of light according to an electric signal. For example, the path adjuster 120 may adjust reflectance to be greater than transmittance when a first electric signal is input, and may adjust reflectance to be less than transmittance when a second electric signal that is different from the first electric signal is input. In another example, the path adjuster 120 may reflect incident light when a first electric signal is input and transmit incident light when a second electric signal is input. The path adjuster 120 may operate like a switchable window. A switchable window may reflect or transmit incident light according to an input electric signal. For example, a switchable window may be formed of a material having adjustable reflection characteristics or transmission characteristics. In another example, the reflection characteristics or transmission characteristics of the switchable window may be mechanically adjustable, for example, by using a shutter.

Figure 4:
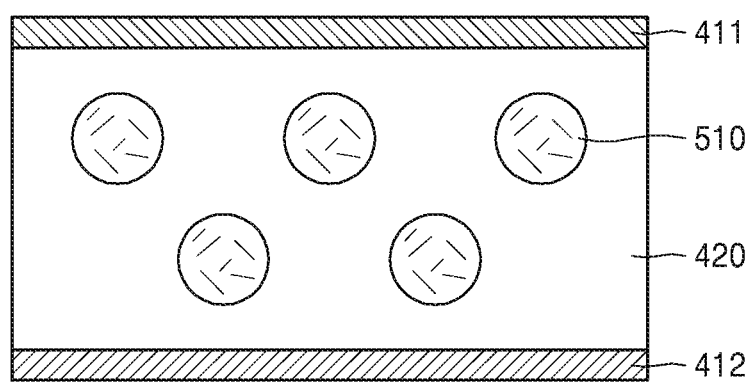
FIG. 4 is a diagram of a path adjuster according to an exemplary embodiment.

The path adjuster 120 may include first and second electrodes 411 and 412 spaced apart from each other, and a reaction portion 420 that reflects or passes light therethrough according to an electric signal, as illustrated in FIG. 4. The reaction portion 420 may include at least one among polymer dispersed liquid crystal (PDLC), twisted nematic (TN) liquid crystal, vertical alignment (VA) liquid crystal, electrically controlled birefringence (ECB) liquid crystal, an electrochromic device, a reflection particle including a reflection plate, and a polar liquid that moves according to an electrowetting phenomenon. A detailed structure of the path adjuster 120 may be described later.

The light receiver 130 may receive a reference light among lights reflected from the path adjuster 120 and receive a measurement light among lights passing through the path adjuster 120. The light receiver 130 may include a depletion layer photodiode, an avalanche photodiode, and a photomultiplier tube. Also, the light receiver 130 may be embodied by a CMOS image sensor or a CCD image sensor. The light receiver 130 may include a plurality of light receivers, and may further include an optical filter corresponding to a predetermined wavelength in each light receiver.

A reference light is light used as a reference for obtaining information about the target material 11, and may be light reflected from the path adjuster 120 among the lights emitted from the light source 110.

Figure 2:
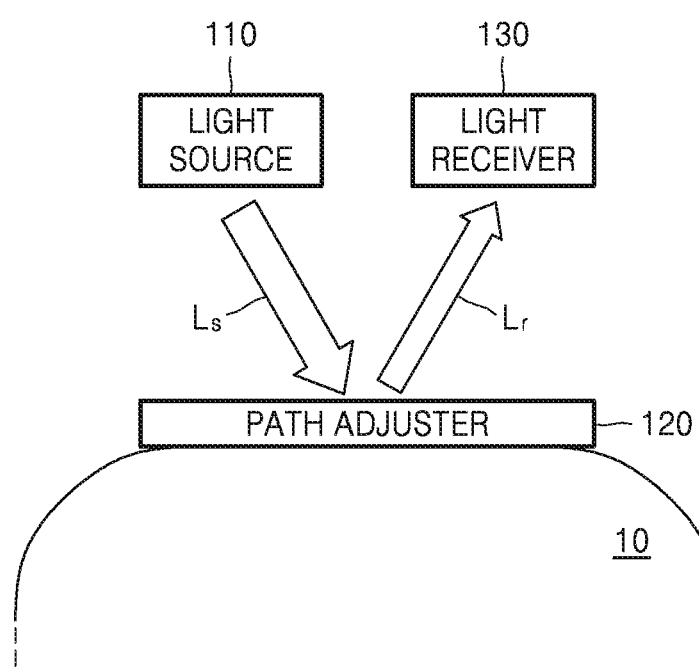
FIG. 2 is a block diagram of the optical sensor of FIG. 1 receiving a reference light.

FIG. 2 is a block diagram of the optical sensor 100a of FIG. 1 receiving a reference light. For example, when a first electric signal, for example, a voltage V1, is applied to the path adjuster 120, the path adjuster 120 reflects incident light $L_s$. The light reflected from the path adjuster 120 becomes a reference light $L_r$. A reflectance of the path adjuster 120 may be 50%. However, exemplary embodiments are not limited thereto. Even when the reflectance of the path adjuster 120 is equal to or less than 50%, the light receiver 130 may receive the light reflected from the path adjuster 120. When the optical sensor 100a receives a reference light, a state of the path adjuster 120 may be referred to as a reference mode.

The measurement light may be light related to the target material 11 and may be light reflected from the target material 11, light passing through the target material 11, or light emitted from a marker coupled with the target material 11. For example, the measurement light may be the light passing through the path adjuster 120 and then reflected from the target material 11, among the lights emitted from the light source 110. Alternatively, the measurement light may be the light passing through the path adjuster 120 and then the target material 11, among the lights emitted from the light source 110. Alternatively, the measurement light may be light emitted from the marker coupled with the target material 11 by the light emitted from the light source 110. The marker may include a fluorescent material, and the light emitted from the marker and the light emitted from the light source 110 may have different center wavelengths. The measurement light may pass through the path adjuster 120 and then be received by the light receiver 130.

Figure 3:
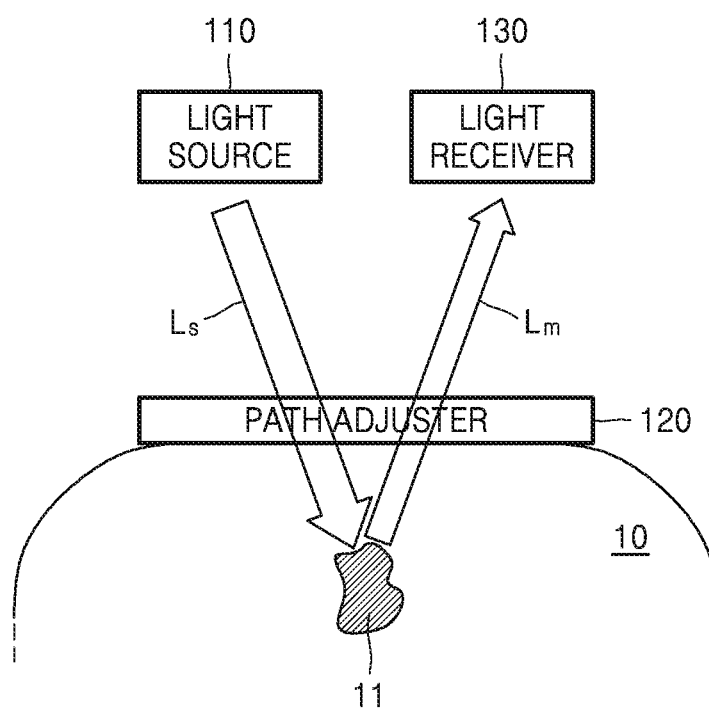
FIG. 3 is a block diagram of the optical sensor of FIG. 1 receiving a measurement light.

FIG. 3 is a block diagram of the optical sensor 100a of FIG. 1 receiving a measurement light. For example, when a second electric signal, for example, a voltage V2, is applied to the path adjuster 120, the path adjuster 120 has incident light $L_s$ passing therethrough. A transmittance of the path adjuster 120 may be 50%, but exemplary embodiments are not limited thereto.

The light passing through the path adjuster 120 may be input in the object 10, and the light input in the object 10 may be reflected from the target material 11 in the object 10. The light reflected from the target material 11 may be a measurement light $L_m$. Although in the drawings for convenience of explanation the light reflected from the target material 11 is illustrated as the measurement light $L_m$, exemplary embodiments are not limited thereto. When the optical sensor 100a receives the measurement light, a state of the path adjuster 120 may be referred to as a measurement mode.

Also, when the transmittance or reflectance of the path adjuster 120 is not 100%, the light receiver 130 may receive the reference light $L_r$ and the measurement light $L_m$ by differentiating light receiving times. For example, the light receiver 130 may receive the reference light $L_r$ at a first time or during a first time period and the measurement light $L_m$ at a second time or during a second time period. At least a partial time period of each of the first time period and the second time period may not be overlapped with each other, or the first time may be different than the second time. By differentiating the light receiving times, noise according to the measurement light $L_m$ may be reduced when the reference light $L_r$ is received, and noise according to the reference light $L_r$ may be reduced when the measurement light $L_m$ is received. Although the light receiver 130 may receive the measurement light $L_m$ after receiving the reference light $L_r$, exemplary embodiments are not limited thereto. The light receiver 130 may receive the reference light $L_r$ after receiving the measurement light $L_m$.

Also, the light receiver 130 may include a plurality of sub-light receivers. For example, the light receiver 130 may include a first light receiver and a second light receiver. The first light receiver may receive the reference light, and the second light receiver may receive the measurement light. The first light receiver and the second light receiver may independently receive the reference light and the measurement light. However, because the lengths of light traveling paths of the measurement light and the reference light are different from each other, a difference in the light receiving time may be generated between the measurement light and the reference light.

The optical sensor 100a according to an exemplary embodiment may receive not only the measurement light, but also the reference light, to obtain the information about the target material 11.

As the optical sensor is miniaturized, the optical sensor may be exposed to various environment changes. For example, when a user tries to measure information about glucose in a body by using the optical sensor, an environment such as temperature or moisture may vary according to whether a measurement place is indoor or outdoor, and also an environment difference may be generated according to whether a measurement time is in the morning or in the afternoon.

Also, as the optical sensor is miniaturized, the light source and the light receiver may be located relatively closer to each other. Accordingly, the light receiver may be affected by heat generated from the light source.

The optical sensor 100a according to an exemplary embodiment may improve accuracy of a detection result by reducing noise according to a change in an environment. The optical sensor 100a according to an exemplary embodiment may receive not only the measurement light but also the reference light reflecting the environment, and may obtain information about a target material by using the reference light and the measurement light.

Figure 5A:
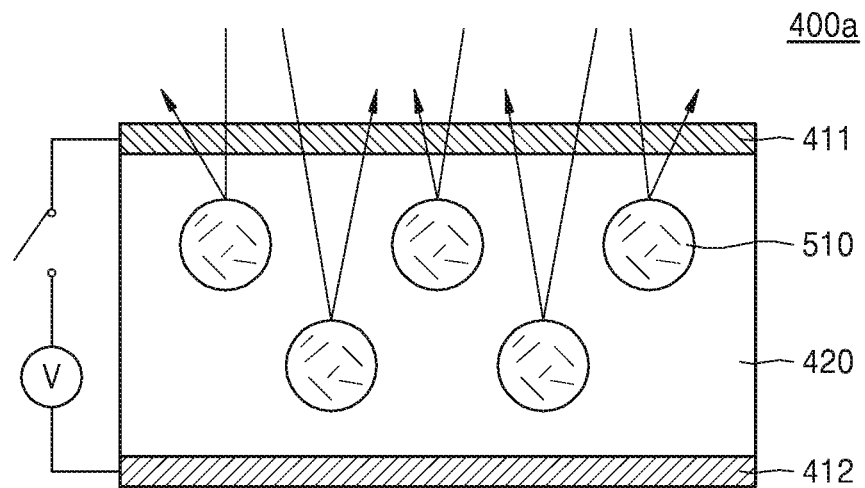
FIG. 5A is a diagram of the path adjuster of FIG. 4 in a reference mode.
Figure 5B:
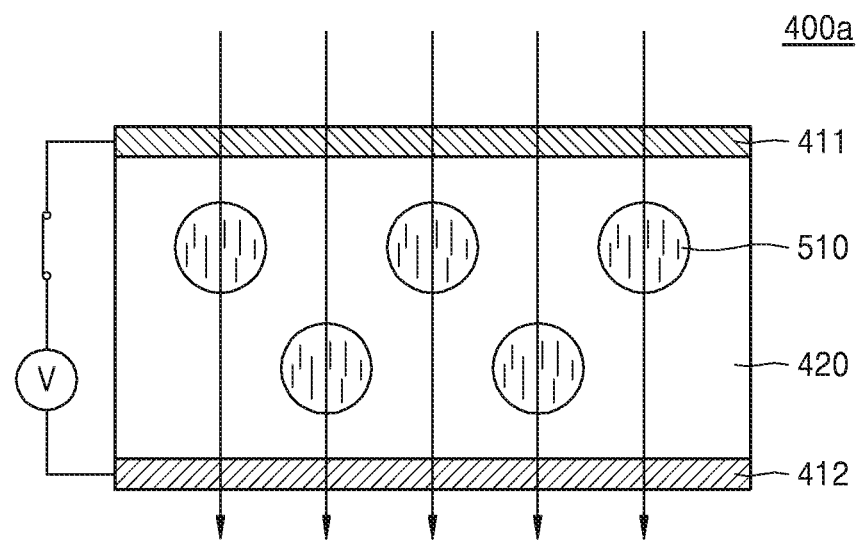
FIG. 5B is a diagram of the path adjuster of FIG. 4 in a measurement mode.

FIG. 4 is a diagram of a path adjuster 400a according to an exemplary embodiment. FIG. 5A is a diagram of the path adjuster 400a of FIG. 4 in a reference mode. FIG. 5B is a diagram of the path adjuster 400a of FIG. 4 in a measurement mode.

As illustrated in FIG. 4, the path adjuster 400a includes the first and second electrodes 411 and 412 spaced apart from each other, and a reaction portion 420 located between the first and second electrodes 411 and 412 and having adjustable transmittance or reflectance.

The first and second electrodes 411 and 412 may be formed of a transparent conductive material. For example, the first and second electrodes 411 and 412 may include a metal oxide such as indium tin oxide (ITO) or indium zinc oxide (IZO), metal nano particles such as Au or Ag dispersed thin film, a carbon nano structure such as carbon nanotube (CNT) or graphene, or a conductive polymer such as poly (3,4-ethylenedioxythiophene) (PEDOT), polypyrrole (PPy), or poly(3-hexylthiophene) (P3HT).

The reaction portion 420 includes polymer dispersed liquid crystal (PDLC) 510 having electrically adjustable transmittance and reflectance to light. The PDLC 510, in a state in which no electric filed is applied characteristically, scatters incident light due to a difference in permittivity between a polymer and liquid crystal. The PDLC 510, in a state in which an electric field is applied characteristically, becomes transparent and passes light as the difference in permittivity between a polymer and liquid crystal oriented according to the electric field decreases. Thus, by adjusting an amount of a voltage applied to the first and second electrodes 411 and 412, the transmittance or reflectance of the reaction portion 420 is adjustable.

For example, as illustrated in FIG. 5A, when no voltage is applied between the first and second electrodes 411 and 412, the light incident on the reaction portion 420 is scattered due to a difference in permittivity between a polymer and liquid crystal, thereby increasing reflectance. In contrast, as illustrated in FIG. 5B, when a voltage is applied between the first and second electrodes 411 and 412, an electric filed is formed in the reaction portion 420. As the liquid crystal is oriented according to the electric filed, the difference in permittivity between a polymer and liquid crystal decreases, and thus the reaction portion 420 becomes transparent. As a result, the transmittance of the reaction portion 420 may increase.

The reaction portion 420 may include not only the PDLC 510, but also twisted nematic (TN) liquid crystal, vertical alignment (VA) liquid crystal, or electrically controlled birefringence (ECB) liquid crystal. Because the above liquid crystals operate similarly to the polymer dispersed liquid crystal, the transmittance or reflectance of the reaction portion 420 is adjustable.

Also, the reaction portion 420 may include an electrochromic device and an electrolyte. The electrochromic device is a material whose color is changed by electrons or holes. In other words, when the electrochromic device is mixed with an electrolyte and an electric field applied thereto, as electrons or holes are combined with a chromic material, a phenomenon that a color appears or disappears may occur. At least one among transmittance and reflectance is adjustable according to an electric signal applied to the first and second electrodes 411 and 412 by using the above phenomenon.

Figure 6:
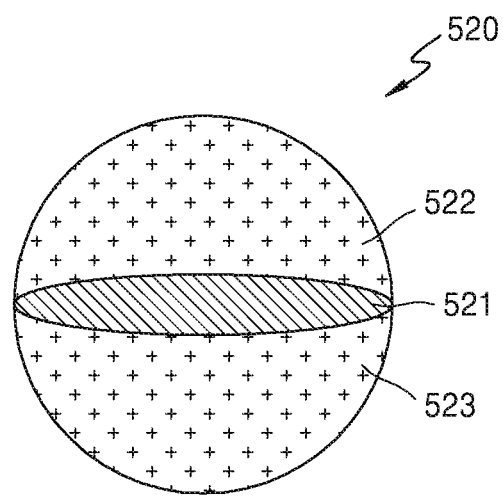
FIG. 6 is a diagram of a reflection particle reflected by a path adjuster included in an optical sensor, according to an exemplary embodiment.
Figure 7A:
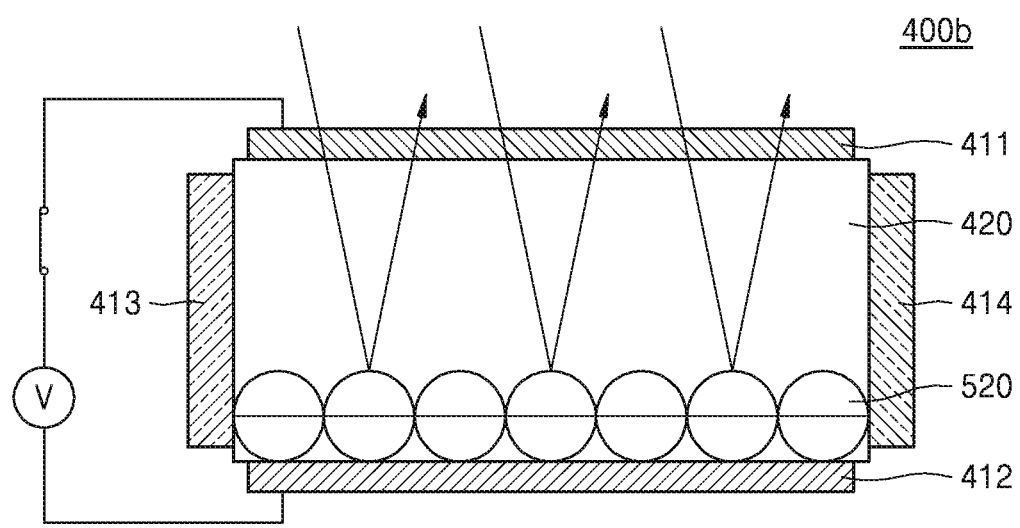
FIG. 7A is a diagram of a path adjuster in a reference mode when the reflection particle of FIG. 6 passes therethrough, according to an exemplary embodiment.
Figure 7B:
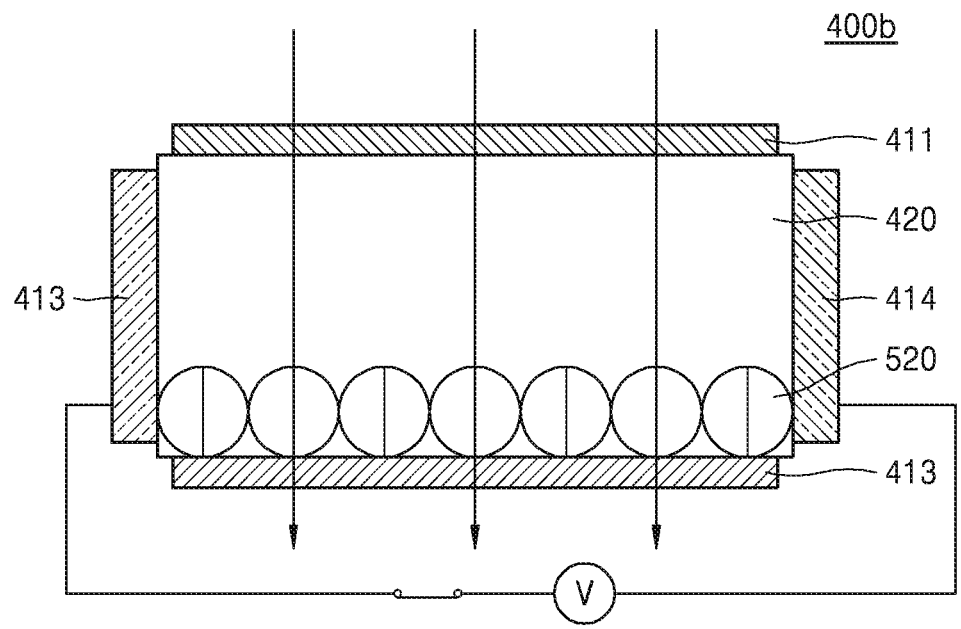
FIG. 7B is a diagram of the path adjuster of FIG. 7A in a measurement mode when the reflection particle of FIG. 6 passes therethrough.

Alternatively, the reaction portion 420 may include a plurality of reflection particles 520 of FIGS. 6, 7A, and 7B, each including a reflection plate 521 for reflecting light and transparent materials 522 and 523 that are charged. Transmittance or reflectance may be adjusted while the reflection particles 520 rotate according to an electric signal.

FIG. 6 is a diagram of the reflection particle 520 reflected by a path adjuster included in an optical sensor, according to an exemplary embodiment. FIG. 7A is a diagram of a path adjuster 400b in a reference mode when the reflection particle 520 of FIG. 6 passes therethrough, according to an exemplary embodiment. FIG. 7B is a diagram of the path adjuster 400b of FIG. 7A in a measurement mode when the reflection particle 520 of FIG. 6 passes therethrough.

As illustrated in FIG. 6, the reflection particle 520 is configured by the reflection plate 521 for reflecting light and the transparent materials 522 and 523 that are charged. The reflection plate 521 may be formed of a material that reflects incident light, whereas the transparent materials 522 and 523 may be formed of a material that passes an incident light therethrough. The transparent materials 522 and 523 may include first and second transparent materials that are charged to opposite polarities with respect to the reflection plate 521. The first and second the transparent materials 522 and 523 may have hemispherical shapes, whereas the reflection plate 521 may have a thin circular disc shape and may be interposed between the first and second the transparent materials 522 and 523.

As illustrated in FIGS. 7A and 7B, the path adjuster 400b includes first to fourth electrodes 411, 412, 413, and 414 encompassing the reaction portion 420. The first and second electrodes 411 and 412 face each other with the reaction portion 420 interposed therebetween, whereas the third and fourth electrodes 413 and 414 face each other with the reaction portion 420 interposed therebetween. The first and second electrodes 411 and 412 may be arranged close to the third and fourth electrodes 413 and 414. The reflection particles 520 are provided in the reaction portion 420. A space in the reaction portion 420 may be filled with a material having the same refractive index as that of the transparent materials 522 and 523.

When an electric signal, for example, a voltage, is applied to the first and second electrodes 411 and 412, as illustrated in FIG. 7A, the reflection plates 521 of the reflection particles 520 may be arranged parallel to surfaces of the first and second electrodes 411 and 412. Accordingly, the light incident on the path adjuster 400b of FIG. 7A is reflected by the reflection plate 521.

When an electric signal, for example, a voltage, is applied to the third and fourth electrodes 413 and 414, the reflection particles 520 rotate and, as illustrated in FIG. 7B, the reflection plate 521 of the reflection particle 520 may be arranged parallel to surfaces of the third and fourth electrodes 413 and 414. Accordingly, the light incident on the path adjuster 400b of FIG. 7B passes through the transparent materials 522 and 523.

Also, the reaction portion 420 may include a polar liquid that moves according to an electrowetting phenomenon. An electrowetting phenomenon signifies that a contact angle of a polar liquid changes when a voltage is applied to the polar liquid on an electrode coated with an insulation material.

Figure 8:
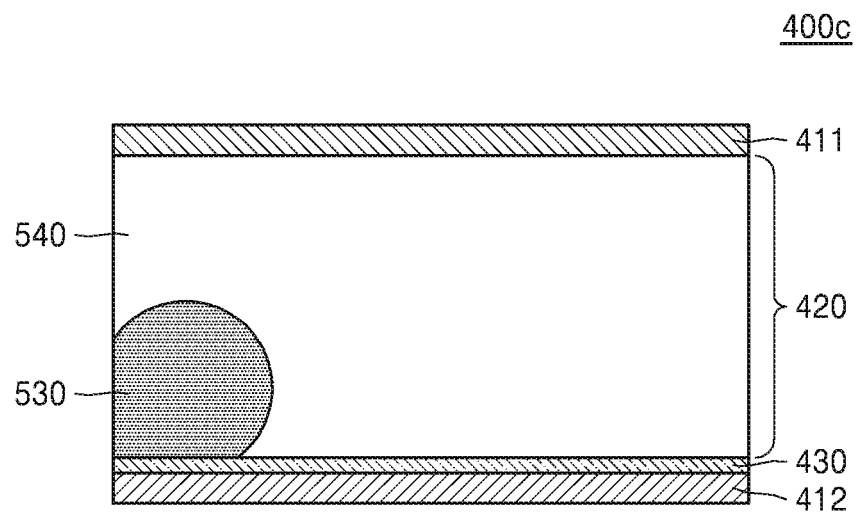
FIG. 8 is a diagram of a path adjuster that operates based on an electrowetting phenomenon, according to an exemplary embodiment.
Figure 9A:
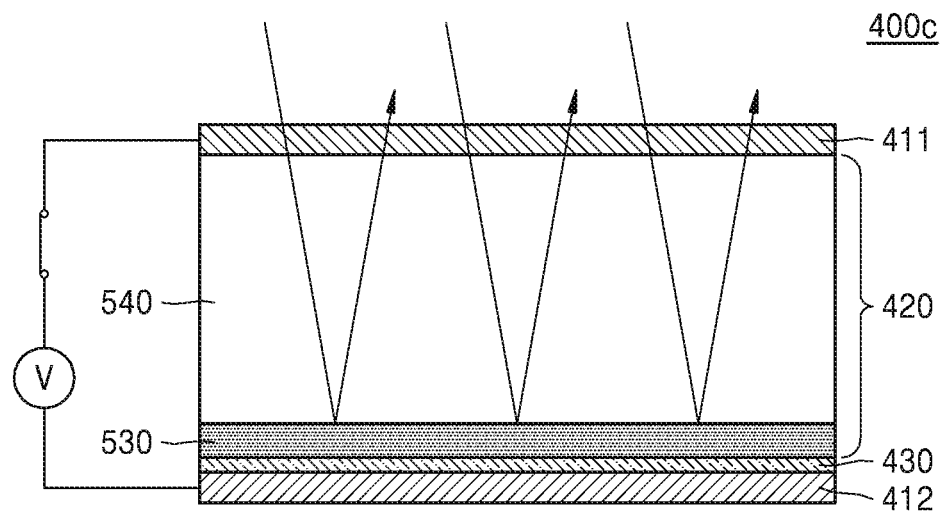
FIG. 9A is a diagram of the path adjuster of FIG. 8 in a reference mode.
Figure 9B:
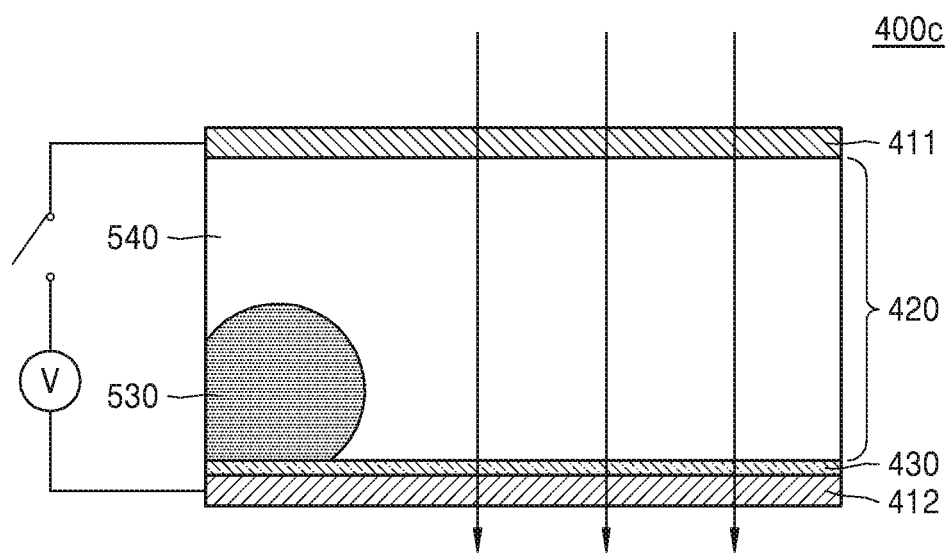
FIG. 9B is a diagram of the path adjuster of FIG. 8 in a measurement mode.

FIG. 8 is a diagram of a path adjuster 400c that operates based on an electrowetting phenomenon, according to an exemplary embodiment. FIG. 9A is a diagram of the path adjuster 400c of FIG. 8 in a reference mode. FIG. 9B is a diagram of the path adjuster 400c of FIG. 8 in a measurement mode.

As illustrated in FIG. 8, the path adjuster 400c includes the first and second electrodes 411 and 412 spaced apart from each other, and the reaction portion 420 including first and second fluids 530 and 540 having different refractive indexes and not mixed with each other. The second electrode 412 is coated with a hydrophobic insulation layer 430.

Any one among the first fluid 530 and the second fluid 540 may be polar, whereas the other one may be non-polar. For example, the first fluid 530 may be a non-transmissive fluid that does not transmit light, for example, a liquid metal or a polar liquid. The second fluid 540 may be a transmissive fluid that is not mixed with the first fluid 530. For example, gas or a non-polar liquid may be employed as the second fluid 540.

Referring to FIG. 9A, when an electrical signal, for example, a voltage, is applied to the first and second electrodes 411 and 412, permittivity increases on a surface of the hydrophobic insulation layer 430, and a droplet of the first fluid 530 spreads over the second electrode 412. Because the first fluid 530 is formed of a non-transmissive material, the light incident on the path adjuster 400c may be reflected.

In contrast, when the application of an electric signal, for example, a voltage, to the first and second electrodes 411 and 412 is discontinued, as illustrated in FIG. 9B, the first fluid 530 is contracted on the hydrophobic insulation layer 430. Accordingly, the light incident on the path adjuster 400c may pass through the second fluid 540 that is transmissive.

The path adjusters 400a, 400b, and 400c may adjust transmittance or reflectance through the arrangement of liquid, molecules, or particles. However, exemplary embodiments are not limited thereto.

A path adjuster 400d may adjust transmittance or reflectance of light by a mechanical movement.

Figure 10A:
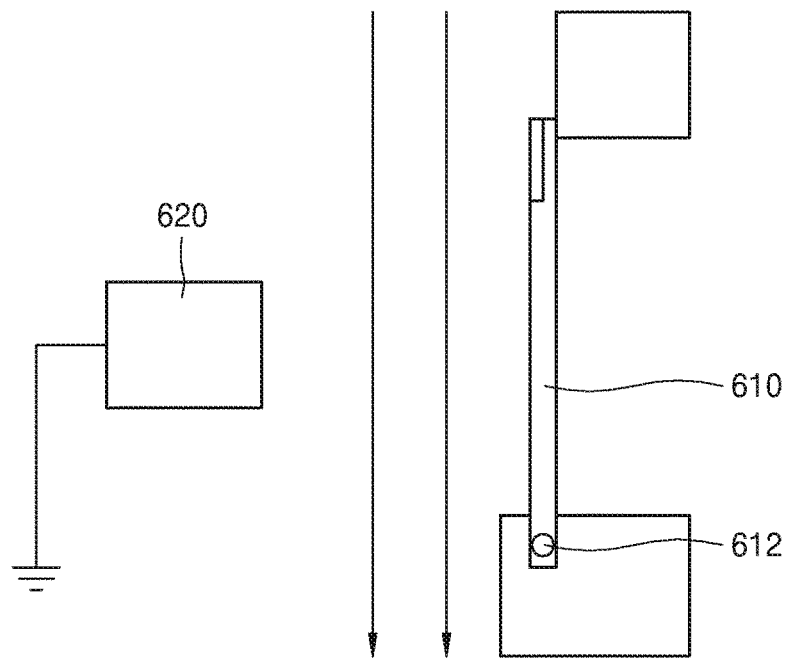
FIGS. 10A and 10B are diagrams of a path adjuster that adjusts a traveling path of light by a mechanical movement, according to an exemplary embodiment.
Figure 10B:
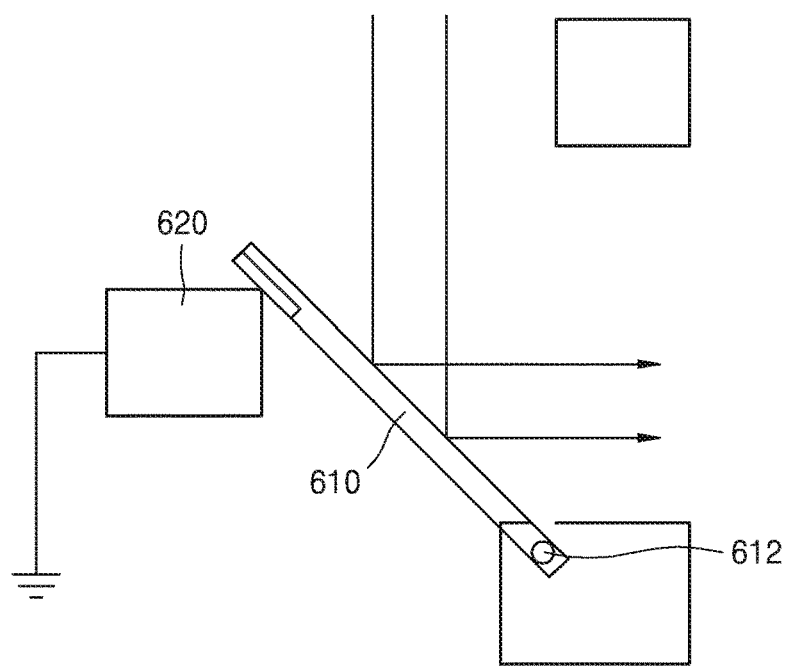

FIGS. 10A and 10B are diagrams of the path adjuster 400d that adjusts a traveling path of light by a mechanical movement, according to an exemplary embodiment.

As illustrated in FIGS. 10A and 10B, the path adjuster 400d includes a reflection plate 610 pivotable around a hinge 612, and an actuator 620 rotating the reflection plate 610. The reflection plate 610 may be a metal film having a high reflectance. The actuator 620 may include a solenoid that generates an electromagnetic force according to an electric signal. As illustrated in FIG. 10A, when no electric signal is applied to the actuator 620, the reflection plate 610 is arranged at a first position. When the reflection plate 610 is arranged at the first position, the light incident on the path adjuster 400d passes through the path adjuster 400d.

In contrast, when an electric signal is applied to the actuator 620, as illustrated in FIG. 10B, the reflection plate 610 is moved to a second position by an electromagnetic force. When the reflection plate 521 is arranged at the second position, the light incident on the path adjuster 400d is reflected from the path adjuster 400d.

The above-described path adjusters 400a, 400b, 400c, and 400d adjust at least one among transmittance and reflectance according to an electric signal. Because the structures of the path adjusters 400a, 400b, 400c, and 400d are examples, exemplary embodiments are not limited thereto, and any device capable of adjusting at least one among transmittance and reflectance may be used as a path adjuster of an optical sensor according to an exemplary embodiment.

A path adjuster 400e may split a traveling path of an incident light without adjusting reflectance or transmittance.

Figure 11:
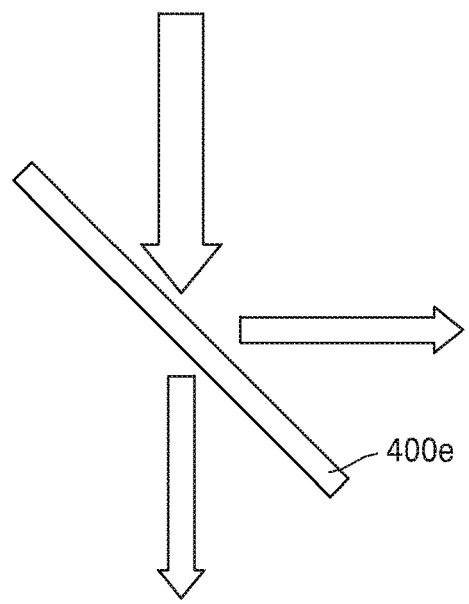
FIG. 11 is a diagram of a path adjuster that adjusts a traveling path of light by splitting light, according to an exemplary embodiment.

FIG. 11 is a diagram of the path adjuster 400e that adjusts a traveling path of light by splitting light, according to an exemplary embodiment. As illustrated in FIG. 11, the path adjuster 400e may reflect part of an incident light and may transmit the other part of the light therethrough. The path adjuster 400e may be a semi-transmissive plate. However, exemplary embodiments are not limited thereto. At least one among the above-described path adjusters may transmit part of light or reflect the other part of the light according to an applied electric signal.

Referring to FIGS. 1 to 3, the light receiver 130 of an optical sensor according to an exemplary embodiment may include a plurality of light receivers.

Figure 12:
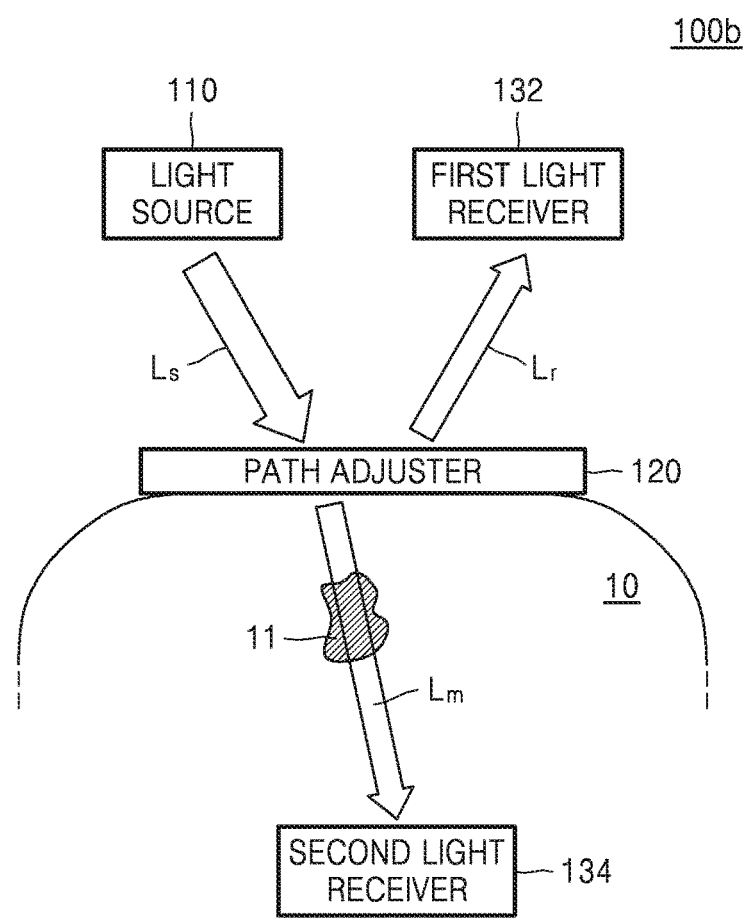
FIGS. 12 and 13 are block diagrams of optical sensors, each including a plurality of light receivers, according to exemplary embodiments.
Figure 13:
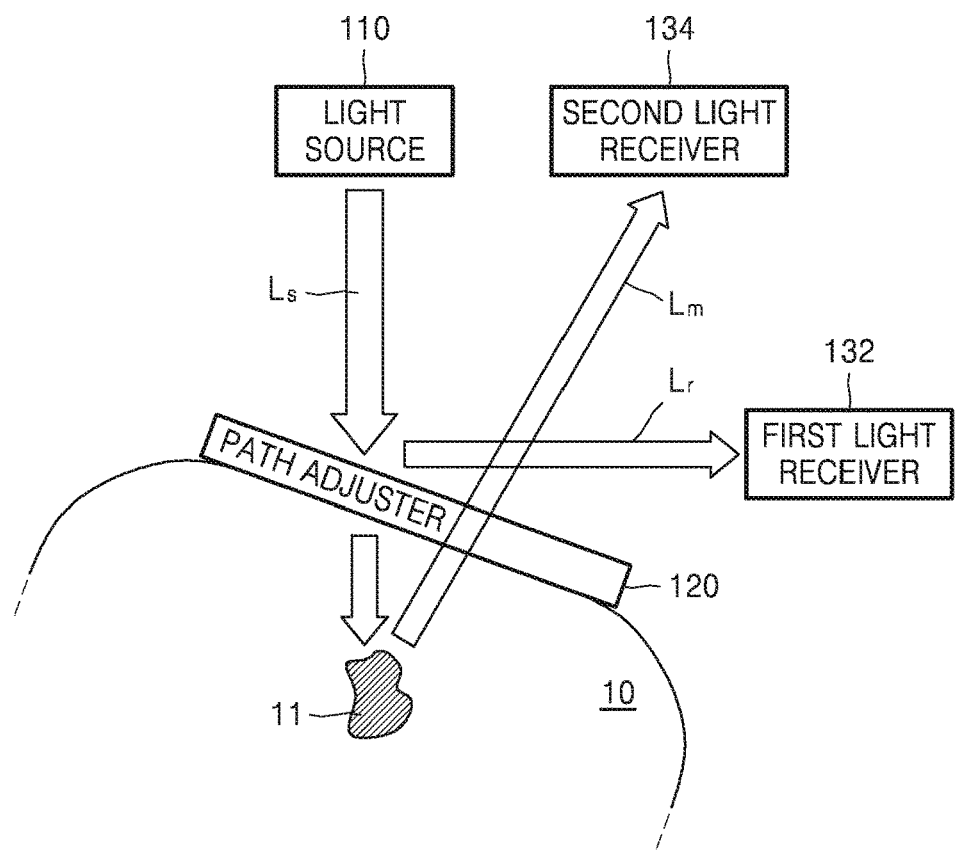

FIGS. 12 and 13 are block diagrams of optical sensors 100b and 100c, each including a plurality of light receivers 132 and 134, according to exemplary embodiments. As illustrated in FIG. 12, when the measurement light $L_m$ is the light passing through the target material 11, the optical sensor 100b includes the first light receiver 132 receiving the reference light $L_r$ among the lights reflected from the path adjuster 120, and the second light receiver 134 receiving the measurement light $L_m$ among the lights passing through the target material 11. Because the lengths of traveling paths of the reference light $L_r$ and the measurement light $L_m$ are different from each other, light receiving times of the first light receiver 132 and the second light receiver 134 may be different from each other.

Also, as illustrated in FIG. 13, the path adjuster 120 reflects part of an incident light and passes the other part of the incident light therethrough. The optical sensor 100c includes the first light receiver 132 receiving the reference light $L_r$ among the lights reflected from the path adjuster 120, and the second light receiver 134 receiving the measurement light $L_m$ among the lights passing through the target material 11, that is, the light passing through the path adjuster 120, reflected from the target material 11, and passing again through the path adjuster 120. Although in FIG. 13 the light reflected from the target material 11 is referred to as the measurement light $L_m$, exemplary embodiments are not limited thereto, and the light passing through the target material 11 may be the measurement light.

The optical sensor may normalize the measurement light using the reference light and the measurement light. The optical sensor may obtain information about the target material using a normalized measurement light. For example, normalization may signify compensation of an influence such as a temperature on the optical sensor by measuring the reference light regularly or irregularly according to a user's request.

Figure 14:
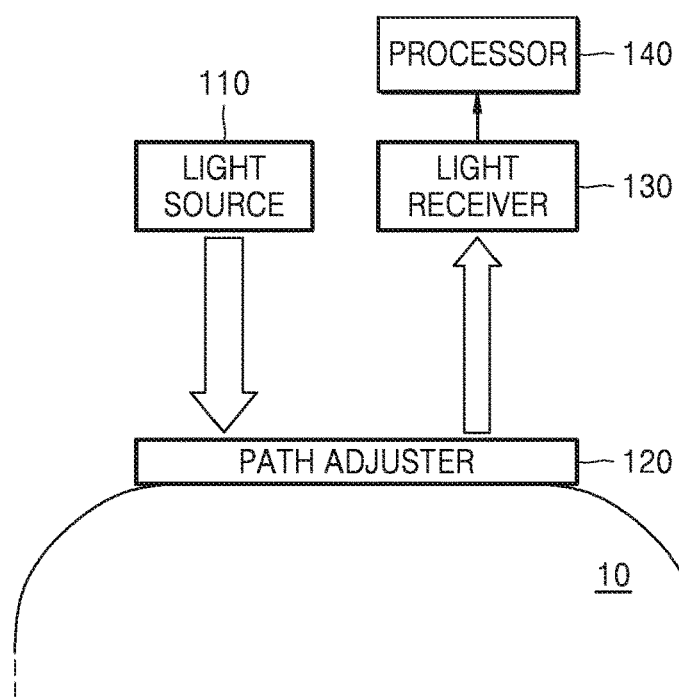
FIG. 14 is a block diagram of an optical sensor according to another exemplary embodiment.

FIG. 14 is a block diagram of an optical sensor 100d according to another exemplary embodiment. As illustrated in FIG. 14, the optical sensor 100d further includes a processor 140 for obtaining the information about the target material 11 by using the reference light and the measurement light.

The processor 140 may normalize the measurement light to obtain the information about the target material 11. As described above, noise may be generated in the optical sensor 100d according to a change in an environment, for example, a change in a temperature and moisture, and a change in performance of the light source 110 and the light receiver 130. To reduce the noise, the optical sensor 100d according to an exemplary embodiment may normalize the measurement light, and thus reliability of a detection result may be improved.

For example, the processor 140 may obtain the normalized measurement light with a ratio of the measurement light to the intensity of the reference light, as expressed in Equation 1 below.

$$I'=I_1/I_0 \qquad \text{[Equation 1]}$$

In Equation 1, "$I_0$" denotes the intensity of the reference light, "$I_1$" denotes the intensity of the measurement light, and "I'" denotes the intensity of the normalized measurement light. As shown in Equation 1, noise in the normalized measurement light is reduced. For example, even when light emission intensity of the light source 110 decreases, not only the intensity of the measurement light but also the intensity of the reference light decreases, and thus the normalized measurement light may be maintained constant. The method of normalizing the measurement light is not limited to Equation 1. For example, the normalization method may vary according to the transmittance or reflectance of the path adjuster 120.

To normalize the measurement light, the processor 140 may use the reference light received at a time close to a time when the measurement light is received. For example, the reference light received just before the measurement light is received or the reference light received just after the measurement light, is received.

The processor 140 may obtain information about the target material, for example, a type of the target material or a change in the concentration of the target material, using the normalized measurement light. To obtain the information about the target material, the processor 140 may use a database including information about the target material matching with light information. For example, the processor 140 may produce absorbance data using the reference light and the measurement light, and the absorbance data may show a changed in the absorbance according to time. Also, the concentration of the target material may be determined using previously stored information about the absorbance. In an example, the information about the absorbance and the concentration of the target material may be stored in the form of a calibration curve.

Next, a result of an experiment to obtain information about the target material using the normalized measurement light is described below.

Exemplary Embodiment 1

An effect of the path adjuster is verified by using the PDLC as the reaction portion of the path adjuster, and Spectralon (Labsphere, Inc.) that reflects 99% of light. When no voltage is applied to the path adjuster, the optical sensor receives the reference light. When a voltage is applied to the path adjuster, the optical sensor receives the measurement light. The optical sensor calculates absorbance of the measurement light received several times, by using the reference light received once.

The processor uses absorbance as expressed in Equation 2 below.

$$A = -\log(I_1/I_0) \quad \text{[Equation 2]}$$

In Equation 2, "A" denotes the absorbance of the target material, and "$I_0$" denotes the intensity of an incident light, which may be obtained from the reference light. "$I_1$" denotes the intensity of a reflected light, which may be obtained from the measurement light.

Figure 15:
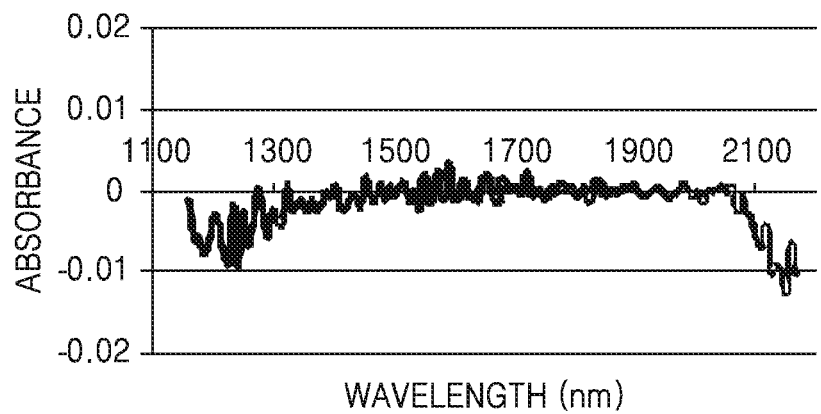
FIG. 15 is a graph showing a result of absorbance obtained by using a reference light that is received once, according to an exemplary embodiment.

FIG. 15 is a graph showing a result of absorbance obtained by using a reference light that is received once, according to an exemplary embodiment. As illustrated in FIG. 15, when absorbance is calculated using one reference light, it is checked that a deviation increases according to a light receiving time or the wavelength of light, even when the same target material is used.

Figure 16:
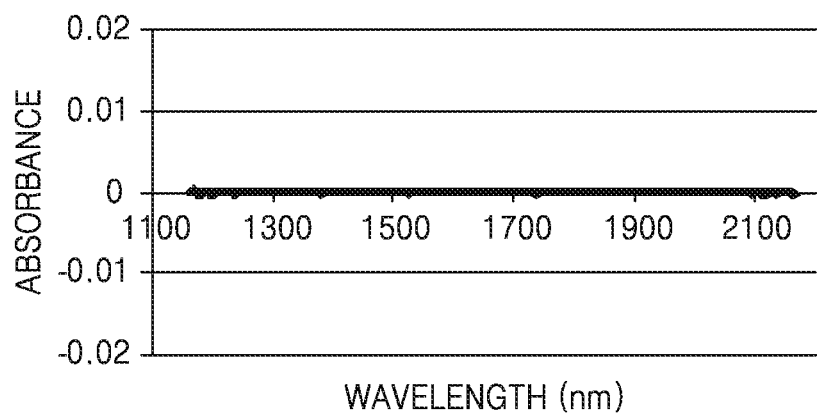
FIG. 16 is a graph showing a result of absorbance obtained by using a reference light and a measurement light that are received successively, according to an exemplary embodiment.

FIG. 16 is a graph showing a result of absorbance obtained by using a reference light and a measurement light that are received successively, according to an exemplary embodiment. The absorbance is obtained by using the reference light and the measurement light that are received each time. The use of the reference light and the measurement light that are received each time signifies a use of a value obtained by dividing the measurement light by the reference light received at an adjacent time, that is, the normalized measurement light. As a result, as illustrated in FIG. 16, it may be checked that the deviation decreases regardless of the light receiving time or the wavelength of light.

The optical sensor may include various constituent elements other than the above-described constituent elements.

Figure 17:
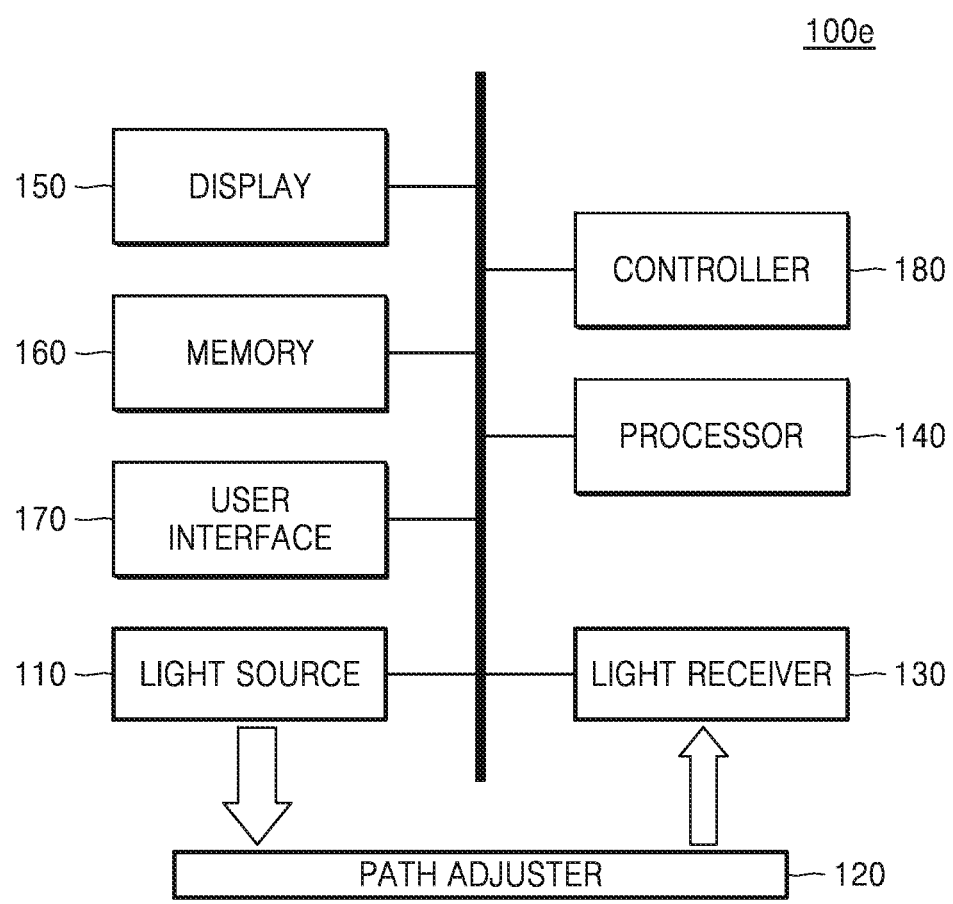
FIG. 17 is a block diagram of an optical sensor according to another exemplary embodiment.

FIG. 17 is a block diagram of an optical sensor 100e according to another exemplary embodiment. As illustrated in FIG. 17, the optical sensor 100e further includes a display 150, a memory 160, a user interface (UI) 170, and a controller 180.

The display 150 may display information processed by the optical sensor 100e. For example, the display 150e may display a UI or a graphic user interface (GUI) to display information about the target material obtained using light. Also, the display 150 may provide a protocol of the optical sensor 100e to a user.

The display 150 may include at least one among a liquid crystal display, a thin film transistor-liquid crystal display, an organic light-emitting diode, a flexible display, and a 3D display. Two or more displays may exist according to an exemplary embodiment of the optical sensor 100e.

The display 150 may form a touch screen in a mutual layer structure with a touch pad to receive a user's input. When the display 150 and a touch pad forming a mutual layer structure are configured to a touch screen, the display 150 may be used as an input device other than an output device. In an exemplary embodiment, the display 150 configured to a touch screen may automatically initiate measurement of the target material as a user's touch input is detected in a predetermined area.

The memory 160 may store data generated during the operation of the optical sensor 100e. The memory 160 according to an exemplary embodiment is a storage medium. The memory 160 may include any of hard disk drives (HDDs), read only memory (ROM), random access memory (RAM), flash memory, and memory cards.

The user interface 170 may receive an input to operate the optical sensor 100e from a user, or may output a type or a concentration change of the target material obtained by the optical sensor 100e. The user interface 170 may include buttons, a keypad, switches, dials, or a touch interface so that a user may directly operation the optical sensor 100e. The user interface 170 may include a display to display an image and may be embodied by a touch screen. In another exemplary embodiment, the user interface 170 may include an I/O port to connect human interface devices (HIDs). The user interface 170 may include an I/O port for input/output of an image.

The controller 180 may control an overall operation of the optical sensor 100e. For example, to obtain information about the target material, the controller 180 may operate the light source 110, the path adjuster 120, the light receiver 130, and the processor 140. For example, the controller 180 may provide an electric signal to the path adjuster 120 to adjust transmittance or reflectance. The controller 180 may control the path adjuster 120 such that reflectance is greater than transmittance, and may control the light source 110 and the light receiver 130 to receive the reference light. The controller 180 may control the path adjuster 120 such that transmittance is greater than reflectance, and may control the light source 110 and the light receiver 130 to receive the measurement light.

The controller 180 may control the light source 110, the path adjuster 120, and the light receiver 130 to alternatively receive the reference light and the measurement light. However, exemplary embodiments are not limited thereto. The controller 180 may control the constituent elements of the optical sensor 100e to receive the reference light once and the measurement light several times at a predetermined time interval. Alternatively, the controller 180 may control the constituent elements of the optical sensor 100e to periodically receive the reference light and receive the measurement light only when a user's command exists.

Also, when obtaining the normalized measurement light, the processor 140 may use the reference light received at a time close to the received measurement light. However, exemplary embodiments are not limited thereto. An average of the already received reference lights may be used. Alternatively, the normalized measurement light may be obtained by using an average of the received measurement lights and an average of the received reference lights. The information about the target material 11 may be obtained by using the normalized measurement light.

As described above, the optical sensor 100e may be embodied by a plurality of apparatuses. For example, the optical sensor 100e may be embodied by a first apparatus including the light source 110 for receiving the reference light and the measurement light, the path adjuster 120, and the light receiver 130 and a second apparatus obtaining information about the target material using the received reference light and measurement light and providing the obtained information about the target material 11. The first apparatus and the second apparatus may be connected to each other by wire or wirelessly. For example, the first apparatus and the second apparatus may perform short-range communication such as Bluetooth or WiFi, or may communicate via a mobile communication network.

The first apparatus may be a wearable device that may be worn by a user. For example, the first apparatus may be a wrist type device that is detachable on a wrist of a user. The second apparatus may be mobile phones, smart phones, desktop computers, laptop computers, tablet PCs, e-book terminals, digital broadcast terminals, personal digital assistants (PDAs), internet protocol televisions (IPTVs), digital televisions (DTVs), or health management servers, but exemplary embodiments are not limited thereto.

Figure 18:
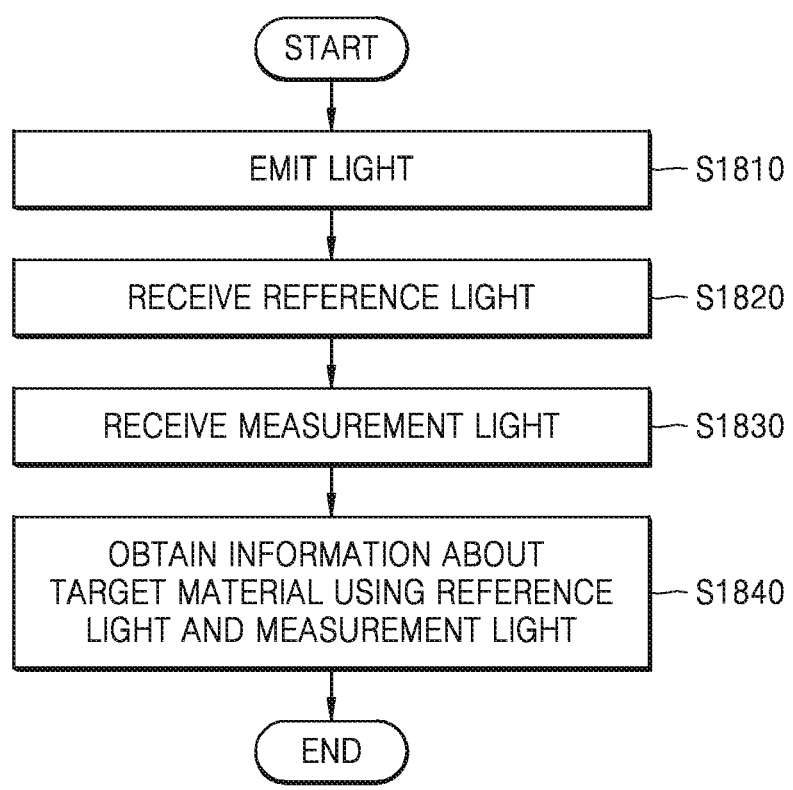
FIG. 18 is a flowchart of a method of operating an optical sensor, according to an exemplary embodiment.

FIG. 18 is a flowchart of a method of operating an optical sensor, according to an exemplary embodiment. Referring to FIG. 18, in operation S1810, the light source 110 emits light. The light source 110 may emit flickering light at a predetermined frequency. Also, the light source 110 may be a surface light source having a large light-emitting area and capable of emitting uniform light so that light may be emitted to an area of the object 10. The light emitted from the light source 110 may vary according to a type of the object or target material. For example, when the object is a human and the target material is a material in a skin of the object, the light source may emit red light or light having a wavelength of a near infrared ray, for example, a center wavelength of about 700 µm to about 1000 µm.

In operation S1820, the light receiver 130 receives a reference light. The reference light may be light that is a reference among the lights reflected from the path adjuster 120. For example, when the path adjuster 120 is in a reflection mode, the light receiver 130 may receive the reference light.

In operation S1830, the light receiver 130 receives a measurement light. The measurement light may be light related to the target material 11 among the lights passing through the path adjuster 120. The measurement light may be light reflected from the target material 11, light passing through the target material 11, or light emitted from a marker coupled with the target material 11. When the path adjuster 120 is in a transmissive mode, the light receiver 130 may receive the measurement light.

A time for receiving the reference light may be different than a time for receiving the measurement light. The light receiver 130 may one-to-one alternately receive the reference light and the measurement light, or may one-to-many or many-to-one alternately receive the reference light and the measurement light. Alternatively, the reference light may be received at a predetermined time interval, and the measurement light may be received only according to a user's command. Also, the light receiver 130 may be divided by a first light receiver for receiving the reference light and a second light receiver for receiving a measurement light.

In operation S1840, the processor 140 obtains information about the target material using the reference light and the measurement light. The processor 140 may normalize the measurement light using the reference light, and obtain the information about the target material using the normalized measurement light. The optical sensor may have high reliability in obtaining the information about the target material, by using the normalized measurement light.

Because the optical sensor according to an exemplary embodiment includes the path adjuster for adjusting a traveling path of light, the reference light and the measurement light may be frequently received. The optical sensor according to an exemplary embodiment may detect the information about the target material using the reference light and the measurement light.

In addition, the exemplary embodiments may also be implemented through computer-readable code and/or instructions on a medium, e.g., a computer-readable medium, to control at least one processing element to implement any above-described exemplary embodiments. The medium may correspond to any medium or media that may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments are examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An optical sensor comprising:
    a light source that emits a light;
    a path adjuster having adjustable transmissivity and reflectivity, and being positionable on a skin of an object so that the path adjuster is disposed between the light source and the skin of the object; and
    a controller configured to:
        selectively control a reflectance of the path adjuster to be greater than a transmittance of the path adjuster at a first time to reflect the light; and
        selectively control the transmittance to be greater than the reflectance for the light to pass through the path adjuster and to be incident on a target material in the skin or blood of the object at a second time different from the first time;
    a light receiver that:
        receives a reference light among the light reflected by the path adjuster; and
        receives, among the light incident on the target material, a first measurement light that is reflected by the target material and passes through the path adjuster; and
    a processor configured to normalize the first measurement light with a ratio of the first measurement light to the intensity of the reference light, and obtain information of the target material based on the normalized measurement light.

2. The optical sensor of claim 1, wherein each of the light reflected by the path adjuster and the light passed through the path adjuster is among the light emitted from the light source.

3. The optical sensor of claim 1, wherein the light receiver further receives a second measurement light that passes through the target material, among the light incident on the target material.

4. The optical sensor of claim 1, wherein the light receiver further receives a second measurement light that is emitted from a marker coupled to the target material, based on the light passed through the path adjuster.

5. The optical sensor of claim 4, wherein a first center wavelength of the second measurement light emitted from the marker is different from a second center wavelength of the light emitted from the light source.

6. The optical sensor of claim 1, further comprising a processor that obtains information of the target material, based on the reference light and the first measurement light.

7. The optical sensor of claim 6, wherein the processor further:
normalizes the first measurement light, based on the reference light; and
obtains the information of the target material, based on the first measurement light that is normalized.

8. The optical sensor of claim 7, wherein the first measurement light that is normalized is a ratio of a first intensity of the first measurement light to a second intensity of the reference light.

9. The optical sensor of claim 1, wherein the light receiver further alternately receives the reference light and the first measurement light.

10. The optical sensor of claim 1, wherein the path adjuster further adjusts either one or both of the reflectance and the transmittance of the path adjuster, based on an electric signal.

11. The optical sensor of claim 10, wherein the path adjuster further:
adjusts the reflectance of the path adjuster to be greater than the transmittance of the path adjuster, in response to a first electric signal; and
adjusts the reflectance of the path adjuster to be less than the transmittance of the path adjuster, in response to a second electric signal different from the first electric signal.

12. The optical sensor of claim 1, wherein the path adjuster comprises:
a first electrode;
a second electrode spaced apart from the first electrode; and
a reaction portion that selectively reflects the light emitted from the light source and allows the light emitted from the light source to pass through the reaction portion, based on an electric signal that is applied between the first electrode and the second electrode.

13. The optical sensor of claim 12, wherein the reaction portion comprises any one or any combination of polymer dispersed liquid crystal, twisted nematic liquid crystal, vertical alignment liquid crystal, electrically controlled birefringence liquid crystal, an electrochromic device, a reflection particle comprising a reflection plate and transparent material, and a polar liquid and a non-polar liquid, the polar liquid moving based on an electrowetting phenomenon.

14. The optical sensor of claim 1, wherein the path adjuster further reflects a first part of the light emitted from the light source and incident on the path adjuster, and allows, to pass through the path adjuster, a second part of the light emitted from the light source and incident on the path adjuster.

15. The optical sensor of claim 1, wherein the light receiver comprises:
a first light receiver that receives the reference light; and
a second light receiver that receives the first measurement light.

16. The optical sensor of claim 1, wherein the path adjuster comprises:
a reflection plate that pivots around a hinge; and
an actuator that selectively rotates the reflection plate to reflect the light emitted from the light source and allows the light emitted from the light source to pass through the path adjuster, based on an electric signal.

17. An optical sensor comprising:
a light source that emits a light;
a path adjuster,
wherein at a first time, a reflectance of the path adjuster is greater than a transmittance of the path adjuster to reflect the light,
wherein at a second time different from the first time, the transmittance is greater than the reflectance for the light to pass through the path adjuster and to be incident on a target material,
wherein the path adjuster comprises:
a reaction portion having a first surface, a second surface facing the first surface, a third surface, and a fourth surface facing the third surface, the reaction portion comprising reflection particles, and each of the reflection particles comprising transparent materials that are charged and a reflection plate disposed between the transparent materials;
a first electrode disposed on the first surface of the reaction portion;
a second electrode disposed on the second surface of the reaction portion;
a third electrode disposed on the third surface of the reaction portion; and
a fourth electrode disposed on the fourth surface of the reaction portion, and
wherein the reflection plate is:
parallel to the first surface and the second surface of the reaction portion to reflect the light, in response to a first electrical signal being applied to the first electrode and the second electrode; and
parallel to the third surface and the fourth surface of the reaction portion to allow the light to pass through the transparent materials, in response to a second electrical signal being applied to the third electrode and the fourth electrode; and
a light receiver that:
receives a reference light among the light reflected by the path adjuster; and
receives, among the light incident on the target material, a first measurement light related to the target material.

18. An optical sensor comprising:
a light source that emits a light;
a path adjuster,
wherein at a first time, a reflectance of the path adjuster is greater than a transmittance of the path adjuster to reflect the light,
wherein at a second time different from the first time, the transmittance is greater than the reflectance for the light to pass through the path adjuster and to be incident on a target material,
wherein the path adjuster comprises:
a first electrode;
a second electrode facing the first electrode;
a hydrophobic insulation layer disposed on the second electrode; and
a reaction portion disposed between the first electrode and the hydrophobic insulation layer, the reaction portion comprising a non-transmissive fluid and a transmissive fluid not mixed with the non-transmissive fluid, and
wherein the non-transmissive fluid:
spreads over the hydrophobic insulation layer to reflect the light, in response to an electrical signal being applied to the first electrode and the second electrode; and
contracts on the hydrophobic insulation layer to allow the light to pass through the transmissive fluid, in response to the electrical signal not being applied to the first electrode and the second electrode; and a light receiver that:
 receives a reference light among the light reflected by the path adjuster; and
 receives, among the light incident on the target material, a first measurement light related to the target material.

19. The optical sensor of claim 1, wherein the path adjuster further comprises:
 a plurality of reflection particles that selectively change the reflectance of the path adjuster to reflect the light emitted from the light source and allow the light emitted from the light source to pass through the path adjuster, based on an electric signal.

* * * * *